United States Patent [19]

Shimazu et al.

[11] Patent Number: 4,875,488
[45] Date of Patent: Oct. 24, 1989

[54] SYSTEM FOR MEASURING THE VOLUME OF A PART OF A HUMAN BODY

[75] Inventors: Hideaki Shimazu, Tokyo; Hiroshi Ito, Kokubunji; Kenichi Yamakoshi, Hokkaido, all of Japan

[73] Assignees: Takashi Inoue; Kabushiki Kaisha Nihon M.D.M., both of Tokyo, Japan

[21] Appl. No.: 188,997

[22] Filed: May 2, 1988

[30] Foreign Application Priority Data

May 13, 1987 [JP] Japan ................. 62-116335

[51] Int. Cl.$^4$ .............................................. A61B 5/02
[52] U.S. Cl. ........................................ 128/694; 128/774
[58] Field of Search ............... 128/694, 693, 774; 73/861.08, 149, 861.12, 861.15, 304 R; 324/65 R, 444, 447, 449; 33/512, 175, 143 L

[56] References Cited

U.S. PATENT DOCUMENTS 2,845,060  7/1958  Roman ......................... 128/672
3,356,942  7/1963  Bennett ......................... 324/65 R

FOREIGN PATENT DOCUMENTS 3516361  11/1986  Fed. Rep. of Germany ...... 128/774
1480470   4/1967  France ............................ 73/149
715986    2/1980  U.S.S.R. ......................... 324/65 R Primary Examiner—Max Hindenburg
Assistant Examiner—Scott Getzow
Attorney, Agent, or Firm—Schwartz & Weinrieb

[57] ABSTRACT

A system for measuring the volume of a part of a human body such as an arm, for diagnostic purposes, is disclosed measuring instrument comprises an outer tube and an inner tube made of flexible material. Both ends of the inner tube are secured to an inside wall of the outer tube so as to form a watertight chamber between the outer tube and the inner tube. Electrodes are provided upon the inside wall of the outer tube, and the watertight chamber is filled with electrolyte. Electric current is passed from one of a pair of electrodes to another electrode through the electrolyte. Voltage across another pair of electrodes is measured so as to measure changes in impedance, thereby detecting changes in the volume of the body part.

9 Claims, 3 Drawing Sheets

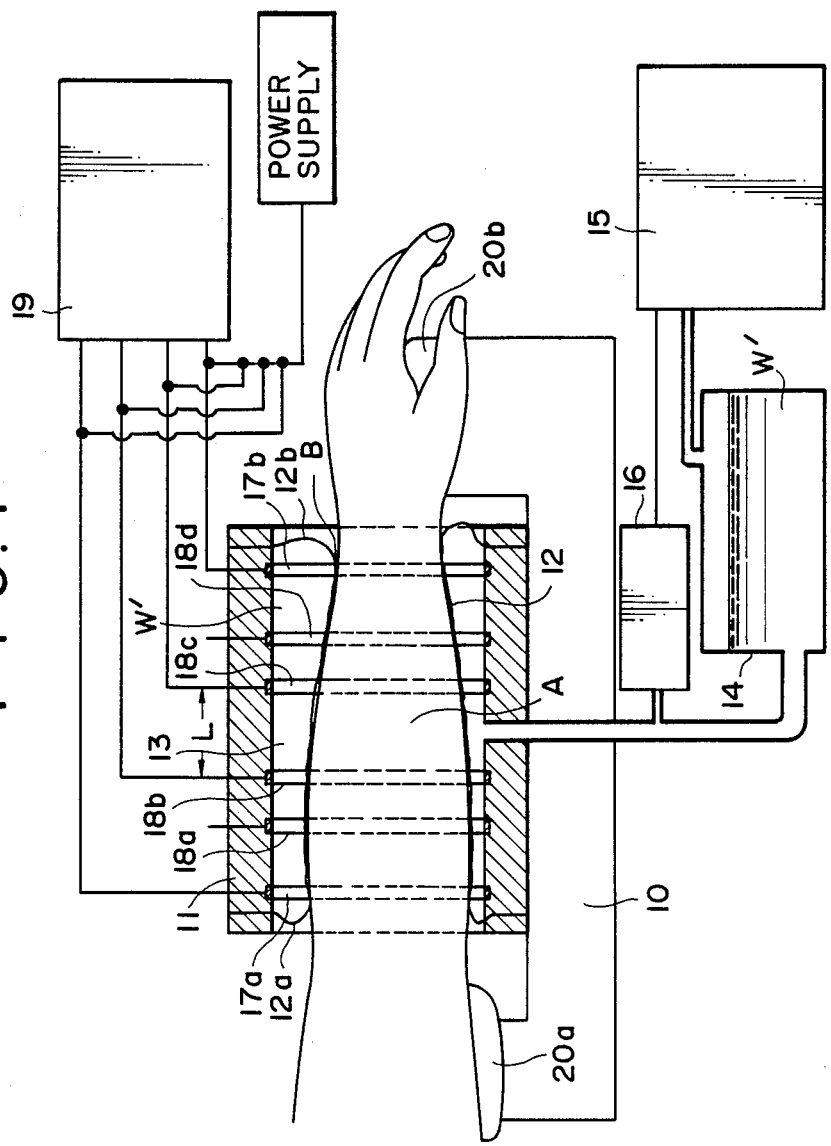

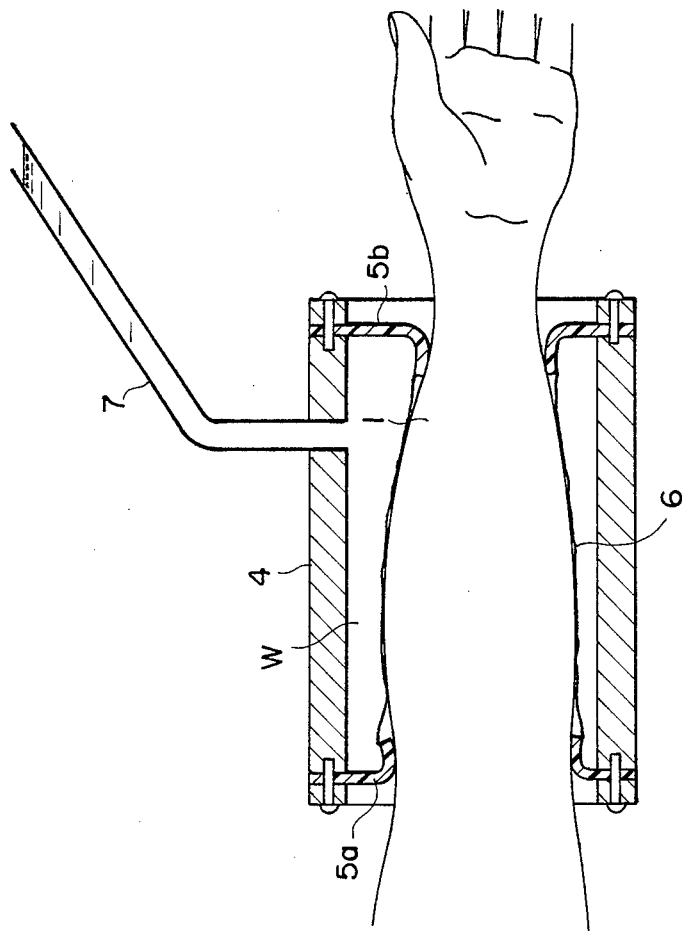

SYSTEM FOR MEASURING THE VOLUME OF A PART OF A HUMAN BODY

FIELD OF THE INVENTION

The present invention relates to a system for measuring the volume of a part of a human body, such as a limb and the head. Change of volume with time represents conditions of the human body. Accordingly, the system is used in various fields such as medical care, preservation of health, sports and others.

BACKGROUND OF THE INVENTION

Heretofore, an instrument called a plethysmograph has been used for measuring changes in the size of a part of the body by measuring changes in the amount of blood in that part. FIGS. 2A and 2B show two examples of the instrument.

In use of one instrument, disposed around a limb, as shown in FIG. 2A, an arm 1 in this case, a pair of current applying wire electrodes 2a and 2b and a pair of voltage detecting wire electrodes 3a and 3b are wound. A predetermined alternating current is applied to the current applying wire electrodes 2a and 2b. Voltage between the voltage detecting wire electrodes 3a and 3b is measured for detecting impedance or admittance between the wire electrodes 3a and 3b. When the volume of the arm 1 between the voltage detecting wire electrodes 3a and 3b becomes large, the impedance there-between decreases, or the admittance increases. Thus, the volume of the body is detected in accordance with a measured value of impedance or admittance.

In use of the other instrument, as shown in FIG. 2B, a cylindrical tank 4 is provided. The tank 4 has an inner flexible tubular member 6 made from a rubber film. End rims of tubular member 6 are supported by means of flexible end flanges 5a and 5b which are fixed to the tank 4. The space between the tank 4 and the inner tubular member 6 is filled with a predetermined amount of water W. When the arm 1 is thrust into the tubular member 6, the member 6 is deformed dependent on the size of the arm 1. Thus, a a portion of the water W disposed about the tubular member 6 overflows through an overflow pipe 7. The amount of the water overflow is measured to obtain the volume of the arm 1.

However, in the case of the former instrument, since wire electrodes are directly attached to the arm 1, high voltage cannot be applied to the current applying wire electrodes 2a and 2b in order to prevent injury to the body. Accordingly, it is impossible to improve the accuracy in the measurements. Furthermore, the operator must be skilled in attaching the wire electrodes to the body.

In the latter case, flexible flanges 5a and 5b are liable to project outwardly as a result of the pressure of the water when the arm 1 is inserted into the tubular member 6, so that the correct amount of water overflowing into the overflow pipe 7 in accordance with the changes of the volume as a result of the arm 1 being inserted cannot be accurately measured.

OBJECT OF THE INVENTION

The object of the present invention is to provide a measuring system which may accurately and simply measure the volume of a part of the body.

SUMMARY OF THE INVENTION

According to the present invention, there is provided a system for measuring the volume of a part of a human body comprising an outer tube made of rigid insulation material, an inner tube made of flexible insulation material and secured to an inside wall of the outer tube at both ends thereof so as to form a tubular portion therein and to form a watertight chamber between the inside wall of the outer tube and the outer wall of the inner tube, and electrodes provided on the inside wall of the outer tube at spaces in an axial direction of the system.

The watertight chamber is filled with electrically conductive liquid.

The system has means for conducting current through the conductive liquid through means of a pair of electrodes selected from the array of electrodes, and means for detecting the voltage across another pair of electrodes.

Thus, the volume of the body part can be measured.

In accordance with one aspect of the invention, at least one of the electrodes is axially slideable upon the inside wall of the outer tube.

In accordance with a further aspect of the invention, means for adjusting the pressure of the liquid is provided.

BRIEF DESCRIPTION OF THE DRAWINGS

These and other objects and features of the present invention will become more apparent from the following detailed description with reference to the accompanying drawings, wherein FIG. 1 is a schematic diagram showing a system for measuring the volume of a part of the human body according to the present invention;

FIG. 2B is a schematic diagram showing a second type of conventional measuring instrument.

DETAILED DESCRIPTION OF THE PREFERRED EMBODIMENT

Figure 2A:
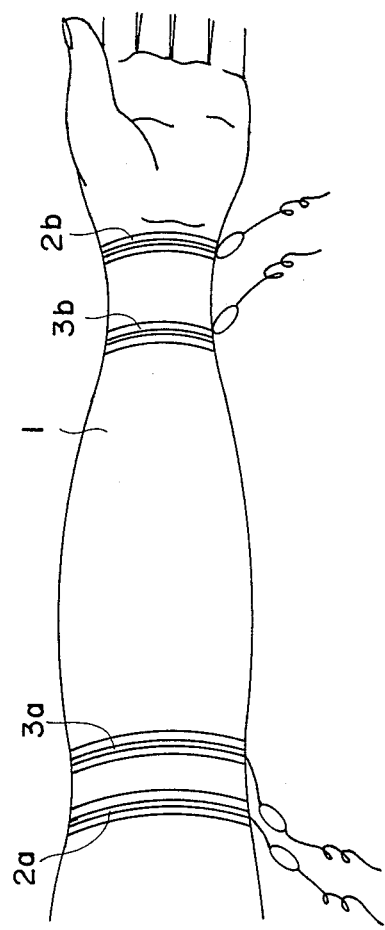
FIG. 2A is a schematic diagram showing one type of a conventional measuring instrument.

Referring to FIG. 1, a system for measuring the volume of a part of the human body according to the present invention comprises a base member 10, a rigid outer tube 11 mounted upon the base member 10, and a flexible inner tube 12 provided inside the outer tube 11. The inner tube 12 has flanges 12a and 12b at both ends thereof and rims of the flanges are secured to the inner wall of the outer tube 11 by means of watertight seals at both end portions of the outer tube. The outer tube 11 is made of insulating material such as acrylic resin. The inner tube 12 is made of rubber and formed so as to define a tubular portion B for receiving an arm A. Between the outer tube 11 and the inner tube 12, a liquid chamber 13 is formed. The liquid chamber 13 is in in communication with an electrolyte tank 14 so as to be supplied with the electrolyte W' therefrom. As electrolyte W', physiological saline solution or a salt solution with a lower concentration than the saline solution is used. A pressure controller 15 is connected to the electrolyte tank 14 at a location above the electrolyte W', and a pressure sensor 16 is provided for detecting the pressure of the electrolyte W' in the liquid chamber 13. In response to a signal from the sensor 16, the controller 15 alters the control pressure to the electrolyte tank 14. Thus, the pressure of electrolyte W' in the liquid chamber 13 is maintained at a predetermined value. Namely, electrolyte tank 14, pressure controller 15, and sensor 16 comprises a liquid pressure control system.

On the inner wall of the outer tube 11, a pair of annular electrodes 17a and 17b are disposed with a predetermined distance therebetween. Furthermore, four annular voltage detecting electrodes 18a, 18b, 18c, 18d are disposed between electrodes 17a and 17b. These annular electrodes are connected to a measuring the instrument 19 for measuring impedance or admittance of the electrolyte W'. Support portions 20a and 20b are formed upon the base member 10 for supporting the arm A.

In order to measure the volume of a part of the arm A, a predetermined amount of the electrolyte W' is supplied to the liquid chamber 13. As the arm A is inserted into the tubular portion B of the inner tube 12, a predetermined alternating current is applied to the electrodes 17a and 17b by means of the power supply PS.

Thereafter, the impedance or admittance of the electrolyte W' between a pair of the voltage detecting electrodes, for example between electrodes 18b and 18c, is measured by means of the measuring instrument 19.

Designating the impedance between the electrodes 18b and 18c as Z, the distance between electrodes 18b and 18c as L, the mean cross-sectional area of the electrolyte W' within the liquid chamber 13 corresponding to the arm portion to be measured as S, and the specific resistance of this electrolyte as $\rho_s$, the impedance Z is represented as $$Z = \rho_s \cdot L / S$$

Thus, the area S is expressed as $$S = \rho_s \cdot L / Z$$

Since the volume $V_s$ of the corresponding electrolyte approximates to S·L, the volume $V_s$ is presented as $$V_s = \rho_s \cdot L^2 / Z$$

Designating the volume of the interior of the outer tube 11 corresponding to the arm portion as $V_T$, the volume V of the arm portion can be expressed as follows $$V = V_T - V_s = V_T - \rho_s \cdot L^2 / Z$$

The small amount of change $\Delta V$ in the volume V of the arm caused by means of changes in the amount of the blood in the arm portion can be represented by the amount of the change $\Delta Z$ in the impedance Z, as follows $$\Delta V = (\rho_s \cdot L^2 / Z^2) \cdot \Delta Z$$

Thus, changes of the volume of a part of the arm can be measured by means of the changes of the impedance of the electrolyte W'.

The pressure controller 15 operates to control the difference between the blood pressure of the arm and the liquid pressure, so that the amount of change $\Delta V$ can be measured under various pressure conditions so as to determine characteristics of the artery and the vein.

In the above example, although the impedance between voltage detecting annular electrodes 18b and 18c has been measured, any two of the voltage detecting electrodes 18a to 18d may be optionally selected in order to measure the changes of the volume of a desired portion of the limb or body part.

Furthermore, it is possible that the annular voltage detecting electrodes be axially slideable upon the outer tube 11 so as to provide a desired distance L between any two electrodes.

Since the admittance is the reciprocal of the impedance, the volume of the arm is measured in the same operation as the measurement by impedance.

In accordance with the present invention, the following effects and advantages are obtained:

(1) Measuring errors as a result of the deformation of the end portions of the inner tube of the instrument are avoided without adversely affecting the compliance or flexibility of the end portions.

(2) It is possible to clearly define the length of a part of the arm to be measured.

(3) By means of the liquid pressure control system, the difference between the blood pressure of the arm and the surrounding pressure within chamber 13 is preferably set.

(4) Since the annular electrodes are not directly attached to the arm, the measuring process is simplified in operation and decreased in operational time. Furthermore, high voltage can be applied to the electrodes without danger of injuring the body, so that the accuracy of the measurement is improved.

(5) Since impedance of the body is not directly measured unlike in the prior art, measurement of the specific resistance of the blood is not required.

While the invention has been described in conjunction with preferred specific embodiments thereof, it will be understood that this description is intended to illustrate and not limit the scope of the invention, which is defined by the following claims.

What is claimed is:

1. A system for measuring the volume of a part of a human body, comprising:
   an outer tube made of a rigid insulation material;
   an inner tube made of a flexible insulation material and secured to an interior wall portion of said outer tube at both ends thereof so as to form a tubular portion therein which defines an annular water-tight chamber between said interior wall portion of said outer tube and an interior wall portion of said inner tube;
   a plurality of electrodes provided upon said interior wall portion of said outer tube at locations spaced along an axial direction of said system;
   electrically conductive liquid provided within said water-tight chamber;
   means for conducting current through said conductive liquid by means of a first pair of said axially spaced electrodes selected from said plurality of electrodes provided upon said interior wall portion of said outer tube; and
   means for detecting voltage across a second pair of said axially spaced electrodes selected from said plurality of electrodes provided upon said interior wall portion of said outer tube,
   whereby when said part of a human body is inserted within said tubular portion of said inner tube and compresses part of said flexible inner tube and said electrically conductive liquid provided within said watertight chamber thereof, an impedance change in said electrically conductive liquid, indicative of said volume of said part of a human body to be measured, can be determined by said voltage detecting means from said voltage across said second pair of axially spaced electrodes.

2. The system according to claim 1 further comprising means for adjusting the pressure of the liquid.

3. A system as set forth in claim 2, wherein said pressure adjusting means comprises:
a liquid reservoir tank having a first outlet fluidically connected to said watertight chamber; and
a pressure controller fluidically connected to a second outlet of said liquid reservoir tank.

4. A system as set forth in claim 3, wherein:
said first outlet of said liquid reservoir tank is disposed within a lower sidewall portion of said liquid reservoir tank so as to be disposed beneath the level of said liquid disposed within said liquid reservoir tank; and
said second outlet of said liquid reservoir tank is disposed within an upper wall portion of said liquid reservoir tank so as to be disposed above said level of said liquid within said liquid reservoir tank.

5. A system as set forth in claim 3, further comprising:
pressure sensing means fluidically connected with said liquid disposed within said watertight chamber for generating a pressure signal to said pressure controller such that said pressure controller can control the pressure of said liquid within said watertight chamber to a predetermined value.

6. A system as set forth in claim 1, wherein:
said human body part is a person's arm.

7. A system as set forth in claim 6, further comprising:
means operatively connected to said outer tube for supporting axially spaced portions of said arm when said arm is disposed within said tubular portion of said inner tube.

8. A system as set forth in claim 7, wherein said supporting means comprises:
a substantially U-shaped support having a forward support portion for supporting a hand portion of said arm, and a rearward support portion for supporting an elbow portion of said arm.

9. A system as set forth in claim 1, wherein:
said plurality of electrodes disposed upon said interior wall portion of said outer tube comprise annular electrodes coaxially disposed with respect to said outer tube.

* * * * *